United States Patent
Talbot et al.

(10) Patent No.: US 10,178,867 B2
(45) Date of Patent: Jan. 15, 2019

(54) TREATING MICROBE CONTAMINATION IN WATER WITH THP SALTS AND POLYMERIC BIOPENETRANTS

(71) Applicant: Solvay Solutions UK Limited, Watford (GB)

(72) Inventors: Robert Eric Talbot, Cannock (GB); Christopher Raymond Jones, Cheslyn Hay (GB)

(73) Assignee: Solvay Solutions UK Limited, Watford (GB)

( * ) Notice: Subject to any disclaimer, the term of this patent is extended or adjusted under 35 U.S.C. 154(b) by 0 days.

(21) Appl. No.: 15/807,315

(22) Filed: Nov. 8, 2017

(65) Prior Publication Data

US 2018/0064112 A1    Mar. 8, 2018

Related U.S. Application Data

(63) Continuation of application No. 14/604,423, filed on Jan. 23, 2015, now abandoned, which is a continuation of application No. 13/745,607, filed on Jan. 18, 2013, now abandoned, which is a continuation of application No. 10/588,474, filed as application No. PCT/GB2005/000373 on Feb. 3, 2005, now abandoned.

(30) Foreign Application Priority Data

Feb. 3, 2004    (GB) .................................. 0402395.8

(51) Int. Cl.
| | | |
|---|---|---|
| *A01N 57/20* | (2006.01) | |
| *A01N 57/34* | (2006.01) | |
| *C02F 5/14* | (2006.01) | |
| *B08B 17/00* | (2006.01) | |
| *C02F 1/50* | (2006.01) | |
| *C23F 11/167* | (2006.01) | |
| *C23F 14/02* | (2006.01) | |
| *C11D 7/36* | (2006.01) | |

(52) U.S. Cl.
CPC ............. *A01N 57/20* (2013.01); *A01N 57/34* (2013.01); *B08B 17/00* (2013.01); *C02F 1/50* (2013.01); *C02F 5/14* (2013.01); *C11D 7/36* (2013.01); *C23F 11/1676* (2013.01); *C23F 14/02* (2013.01); *A01N 2300/00* (2013.01); *C02F 2305/04* (2013.01)

(58) Field of Classification Search
CPC ............ A01N 57/20; A01N 57/34; C02F 5/14
See application file for complete search history.

(56) References Cited

FOREIGN PATENT DOCUMENTS

| EP | 0861846 A2 * | 9/1998 | ................ C07F 9/48 |
| WO | WO-9933345 A1 * | 7/1999 | ............. A01N 57/34 |
| WO | WO-0021892 A1 * | 4/2000 | ................ C02F 5/14 |

* cited by examiner

Primary Examiner — Theodore R. West

(57) ABSTRACT

A synergistic composition comprising a THP salt and a biopenetrant, in which the biopenetrant comprises a polymer of an unsaturated carboxylic acid or a copolymer of an unsaturated carboxylic acid with a sulphonic acid, said polymer or copolymer being terminated by a mono- or diphosphonated unsaturated carboxylic acid group or having such monomers incorporated into the polymer backbone. This composition acts synergistically to enhance the biocidal efficacy of the THP salt against both planktonic (free-swimming) and sessile (attached) bacteria, and also acts synergistically to enhance the efficacy of the THP salt in the dissolution of iron sulphide scale.

18 Claims, No Drawings

TREATING MICROBE CONTAMINATION IN WATER WITH THP SALTS AND POLYMERIC BIOPENETRANTS

This application is continuation of U.S. application Ser. No. 14/604,423, filed Jan. 23, 2015, which is a continuation of U.S. application Ser. No. 13/745,607, filed Jan. 18, 2013, now abandoned, which is a continuation of U.S. application Ser. No. 10/588,474, filed Nov. 14, 2008, now abandoned, which is a national phase application under 35 U.S.C. § 371 of PCT International Application PCT/GB2005/000373, filed Feb. 3, 2005, which claims priority under 35 U.S.C. § 119 of GB 0402395.8, filed Feb. 3, 2004. The entire contents of these applications are hereby expressly incorporated by reference.

This invention relates to synergistic biocidal or metal sulphide dissolving compositions.

The present invention is a selection invention relative to our published P.C.T. application WO 99/33345.

The said WO 99/33345 discloses synergistic biocidal compositions comprising "THP", a non-surfactant biopenetrant compatible with "THP" and optionally a surfactant.

The term "THP" is defined in WO 99/33345 as meaning either a tetrakis(hydroxyalkyl)phosphonium salt or a tris(hydroxyalkyl)phosphine. To avoid confusion we shall hereinafter refer to "THP salts" or "THP" respectively.

Examples of non-surfactant biopenetrants disclosed in the said WO 99/33345 include phosphonated derivatives of carboxylic acids, for example the phosphonated telomers disclosed in our published European applications EP-A-0 491 391 and EP-A-0 861 846.

Other non-surfactant biopenetrants disclosed in the said WO 99/33345 include a copolymer of N, N, N', N'-tetramethyl-1,2-diaminoethane with bis(2-chloroethyl)ether. This is commercially available under the trade name WSCP and will hereinafter be so referred to.

Where surfactants are used, examples disclosed in the said WO 99/33345 include sulphonated (anionic) surfactants and cationic surfactants such as those based on quaternary ammonium compounds, as well as non-ionic, amphoteric and semi-polar surfactants.

We have now unexpectedly found that where the biopenetrant is a phosphonic acid-tipped polymer or copolymer, it acts synergistically with a THP salt to considerably enhance the biocidal efficacy of the THP salt against both planktonic (free-swimming) and sessile (attached) bacteria.

It has also unexpectedly been found that where the biopenetrant is a phosphonic acid-tipped polymer or copolymer, it acts synergistically with a THP salt to enhance the efficacy of the THP salt in the dissolution of metal sulphide, especially iron sulphide, scale.

Accordingly, the present invention provides a synergistic composition comprising:
(i) a THP salt (as hereinbefore defined) and
(ii) a biopenetrant
in which the biopenetrant comprises a polymer of an unsaturated carboxylic acid or a copolymer of an unsaturated carboxylic acid with a sulphonic acid, said polymer or copolymer being either terminated by a mono-or di-phosphonated unsaturated carboxylic acid or having such monomers incorporated into the polymer backbone.

The synergistic composition may be a synergistic biocidal composition and/or a synergistic metal sulphide (e.g. iron sulphide) dissolving composition.

Preferably, the THP salt is tetrakis(hydroxymethyl)phosphonium sulphate (THPS). Other THP salts include the phosphite, bromide, fluoride, chloride, phosphate, carbonate, acetate, formate, citrate, borate, and silicate.

The biopenetrant may comprise a polymer of an unsaturated carboxylic acid or a copolymer of an unsaturated carboxylic acid with a sulphonic acid, said polymer or copolymer being either terminated by vinylphosphonic acid (VPA) or vinylidene-1, 1-diphosphonic acid (VDPA) or having such monomers incorporated into the polymer backbone; accordingly the biopenetrant may be a random copolymer incorporating VPA and/or VDPA monomers.

The polymer or copolymer of the biopenetrant may suitably be a polyacrylate or an acrylate/sulphonate copolymer.

In accordance with preferred embodiments of the present invention, the biopenetrant may be a polyacrylate terminated with vinylphosphonic acid, (hereinafter "VPA end-capped polymer") or with vinylidene-1, 1-diphosphonic acid (hereinafter "VDPA end-capped polymer"), or may be a polyacrylate incorporating VPA and/or VDPA monomers.

In other preferred embodiments, the biopenetrant may be an acrylate/sulphonate copolymer terminated with vinylidene-1, 1-diphosphonic acid (hereinafter "VDPA end-capped copolymer") or with vinylphosphonic acid (hereinafter "VPA end-capped co-polymer"), or may be an acrylate/sulphonate copolymer incorporating VPA and/or VDPA monomers.

In the composition of the present invention, the preferred ratio of VPA or VDPA end-capped polymer or copolymer to THP salt, is, when expressed as a percentage by weight, in the range of from 0.5 to 50%, such as from 0.5 to 30%; preferably from 1 to 25%, such as from 1 to 20%, for example from 1 to 10% or from 2 to 8%; most preferably from 1 to 5%, for example from 3 to 5% (based upon active solids and upon a 1 to 74%, for example a 50%, active THP salt formulation).

In one embodiment, the biopenetrant is a VPA end-capped polymer or VDPA end-capped copolymer.

The preferred ratio of VPA end-capped polymer or VDPA end-capped copolymer to THP salt is, when expressed as a percentage by weight, in the range of from 0.5 to 50%, such as from 0.5 to 30%; preferably from 1 to 25%, such as from 1 to 20%, for example from 1 to 10% or from 2 to 8%; most preferably from 1 to 5%, for example from 3 to 5% (based upon active solids and upon a 1 to 74%, for example a 50%, active THP salt formulation).

The composition may, in one embodiment, be provided in the form of a solution, for example an aqueous solution.

Alternatively the composition may be supplied as a solid, for example a solid formed by coating the components onto, or absorbing the components into, a powdery granular or porous acid substrate such as adipic acid or by incorporation into a waxy substrate.

As noted above, the compositions according to the present invention may be used as biocides against both planktonic (free-swimming) and sessile (attached) bacteria.

We have found that the compositions according to the present invention are equally effective in reducing the level of general heterotrophic bacteria and of sulphate reducing bacteria in waters.

The invention therefore also provides a method of treating a water system contaminated, or liable to contamination, with microbes such as bacteria, fungi or algae, which method comprises adding to said system separately or together, a biocidally active amount of a THP salt and a biopenetrant, in which the biopenetrant comprises a polymer of an unsaturated carboxylic acid or a copolymer of an unsaturated carboxylic acid with a sulphonic acid, said polymer or copolymer being terminated by a mono- or di-phosphonated unsaturated carboxylic acid group or being a random copolymer containing a mono or di-phosphonated unsaturated carboxylic acid, thereby killing at least some of said microbes.

The water system may, for instance, be contaminated with bacterial slime and/or planktonic bacteria. The invention may be of use for treating aerobic systems such as cooling towers, paper processing systems and waste water systems, and also for anaerobic systems, such as oil wells, e.g. during secondary recovery. The invention may also be suitable for use in the preservation of slurries and functional fluids, such as drilling muds, completion fluids, stimulation fluids and fracturing fluids.

As mentioned above, the compositions according to the present invention may also be used to dissolve metal sulphides, preferably iron sulphide; in particular they may be used to dissolve iron sulphide scale. However, the metal sulphide may be lead sulphide or zinc sulphide or a combination of iron or lead and zinc sulphides.

The iron sulphide may typically be troilite (FeS) or pyrite ($FeS_2$), but any iron sulphide species can be dissolved using the invention.

The invention therefore also provides a method of treating a water system containing or in contact with a metal sulphide scale, for example an iron sulphide scale, which method comprises adding to said system separately or together, a THP salt and a biopenetrant, in which the biopenetrant comprises a polymer of an unsaturated carboxylic acid or a copolymer of an unsaturated carboxylic acid with a sulphonic acid, said polymer or copolymer being terminated by a mono- or di-phosphonated unsaturated carboxylic acid group or being a random copolymer containing a mono or di-phosphonated unsaturated carboxylic acid, thereby dissolving at least part of said scale.

The invention may be of use in the oil and gas industry, for treating systems such as oil wells, gas wells, pipelines, storage vessels and production equipment, e.g. during secondary recovery, and in other industrial water systems, for instance in paper industry systems.

The present invention will be illustrated by way of the following examples.

In the examples, the various abbreviations have the following meaning:
VPA polymer: a vinylphosphonic acid-terminated polyacrylate of molecular weight about 4000
VDPA copolymer: a vinylidene-diphosphonic acid-terminated acrylate/sulphonate copolymer of molecular weight 5000-6000
GHB: general heterotrophic bacteria
SRB: sulphate reducing bacteria
WHO water: World Health Organisation Standard Hardness Water (see TABLE I below)
SMOW water: Standard Mean Ocean Water (see TABLE II below)
THPS: a 50% aqueous solution of tetrakis(hydroxymethyl) phosphonium sulphate
WSCP: copolymer of N, N, N', N'-tetramethyl-1,2-diamino ethane and bis(2-chloroethyl)ether.

TABLE I

WHO Standard Hardness Water 1 litre contains:

| | |
|---|---|
| $CaCl_2$ (anhydrous) | 0.305 g |
| $MgCl_2 \cdot 6H_2O$ | 0.139 g |

TABLE II

Standard Mean Ocean Water 5 litres contain:

| | |
|---|---|
| NaCl | 122.65 g |
| $MgCl_2 \cdot 6H_2O$ | 55.52 g |
| $Na_2SO_4$ | 20.45 g |
| $CaCl_2 \cdot 2H_2O$ | 7.69 g |
| KCl | 3.48 g |
| $NaHCO_3$ | 1.00 g |
| KBr | 0.50 g | pH adjusted to 8.2 by means of 0.1N NaOH

EXAMPLE 1

Quantitative Suspension Test (Planktonic Bacteria) in WHO Water

| | Log Reduction of General Heterotrophic Bacteria (based upon 50 ppm ai THPS) Contact period | |
|---|---|---|
| Test Product | 1 hour contact | 3 hour contact |
| Control | 0 | 0 |
| Unformulated THPS | 1 | 5.8 |
| THPS/VPA polymer* | 7.4 | Total kill |
| THPS/VDPA polymer* | 7.4 | Total kill |
| THPS/0.7% WSCP | 3.7 | 7.4 |

EXAMPLE 2

Quantitative Suspension Test in De Inking Water

| | Log reduction values for 75 ppm ai THPS/3 hour contact | |
|---|---|---|
| Test Product | GHB | SRB |
| Control | 0 | 0 |
| Unformulated THPS | 3.8 | 3 |
| THPS/VPA polymer* | 5.1 | 3 |

EXAMPLE 3

Biofilm (Sessile) Tests: Freshwater (WHO)

| Test Product | Viable bacteria (GHB) after 75 ppm ai THPS dosed for 3 hours |
|---|---|
| Control | $1 \times 10^5$ |
| Unformulated THPS | $1 \times 10^5$ |
| THPS/VPA polymer* | $1 \times 10^2$ |
| THPS/VDPA polymer* | <10 |
| THPS/2% sulphonated surfactant (a) | $1 \times 10^3$ |

EXAMPLE 4

Biofilm Tests: Seawater (SMOW)

| Test Product | Viable bacteria after 75 ppm ai THPS dosed for 3 hours | |
|---|---|---|
| | GHB | SRB |
| Control | $1 \times 10^4$ | $1 \times 10^6$ |
| Unformulated THPS | $1 \times 10^2$ | $1 \times 10^4$ |
| THPS/VPA polymer* | <10 | <10 |
| THPS/VDPA polymer* | $1 \times 10^2$ | $1 \times 10^2$ |
| THPS/5% quaternary ammonium compound(b) | $1 \times 10^2$ | $1 \times 10^3$ |

*In each case, the ratio of THPS to "polymer" was 50% a.i. THPS to 5% "polymer", the "polymer" comprising 25% solids as the sodium salt.

(a) A di-sodium salt of a mixed mono- and di-alkyl disulphonated diphenyl oxide, available as DOWFAX® 2A1.

(b) An alkyl dimethyl benzyl ammonium chloride, available as EMPIGEN®BAC 50.

EXAMPLE 5

Iron Sulphide Dissolution Tests

The following solutions were made:
(a) THPS:—THPS (26.6g)+de-ionised water (73.4g)
(b) VPA polymer:—VPA polymer solution having 20% active ingredient (20g)+de-ionised water (80g)
(c) VDPA polymer:—VDPA polymer solution having 20% active ingredient (20g)+de-ionised water (80g)
(d) THPS/5% VPA polymer:—THPS (26.6g)+VPA polymer solution having 20% active ingredient (5g)+de-ionised water (68.4g)
(e) THPS/5% VDPA polymer:—THPS (26.6g)+VDPA polymer solution having 20% active ingredient (5g)+de-ionised water (68.4g)
(f) THPS/20% VPA polymer:—THPS (26.6g)+VPA polymer solution having 20% active ingredient (20g)+de-ionised water (53.4g)
(g) THPS/20% VDPA polymer:—THPS (26.6g)+VDPA polymer solution having 20% active ingredient (20g)+de-ionised water (53.4g)

To each of these solutions was added 2g (accurately weighed) of an iron sulphide field scale (from a water injection system). The solutions were then stirred in a heated water bath for 20 hrs at 50° C., after this time they were filtered through a weighed filter paper. The filter paper and solids were then allowed to dry before re-weighing; the weight of solids remaining was therefore determined, and the % weight loss calculated.

The iron concentrations in the filtered solutions were also measured using the iron method on the Hach DR2000 spectrophotometer.

| Dissolver | pH | % wt loss | $Fe^{2+}$ concentration in solution ppm |
|---|---|---|---|
| (a) THPS | 3.23 | 63 | 3120 |
| (b) VPA polymer | 4.54 | 60 | 1310 |
| (c) VDPA polymer | 3.28 | 47 | 1430 |
| (d) THPS + 5% VPA polymer | 3.77 | 74 | 3320 |
| (e) THPS + 5% VDPA polymer | 3.13 | 78 | 3560 |
| (f) THPS + 20% VPA polymer | 3.94 | 76 | 3480 |
| (g) THPS + 20% VDPA polymer | 2.99 | 83 | 5260 |

The invention claimed is:

1. A method of treating a freshwater system contaminated with microbes, the method comprising the step of adding to said system separately or together, a biocidally active amount of a THP salt and a biopenetrant, wherein the biopenetrant comprises a copolymer of an unsaturated carboxylic acid with a sulfonic acid, said copolymer being terminated by vinylidene-1,1-diphosphonic acid (VDPA) or having such monomers incorporated into the polymer backbone, thereby killing at least some of said microbes.

2. The method according to claim 1, wherein the THP salt is tetrakis(hydroxymethyl) phosphonium sulfate.

3. The method according to claim 1, wherein the THP salt is a tetrakis(hydroxymethyl) phosphonium phosphite, a tetrakis(hydroxymethyl) phosphonium bromide, a tetrakis(hydroxymethyl) phosphonium fluoride, a tetrakis(hydroxymethyl) phosphonium chloride, a tetrakis(hydroxymethyl) phosphonium phosphate, a tetrakis(hydroxymethyl) phosphonium carbonate, a tetrakis(hydroxymethyl) phosphonium formate, a tetrakis(hydroxymethyl) phosphonium citrate, a tetrakis(hydroxymethyl) phosphonium borate or a tetrakis(hydroxymethyl) phosphonium silicate.

4. The method according to claim 1, wherein the copolymer of the biopenetrant is an acrylate/sulfonate copolymer.

5. The method according to claim 4, wherein the acrylate/sulfonate copolymer has a molecular weight of 5000-6000.

6. The method according to claim 1, wherein the proportion of the VDPA copolymer to THP salt is from 1% to 50% by weight, relative to the total weight of the composition.

7. The method according to claim 6, wherein the proportion is from 1% to 25% by weight, relative to the total weight of the composition.

8. The method according to claim 7, wherein the proportion is from 1% to 5% by weight, relative to the total weight of the composition.

9. The method of claim 1, wherein the microbes are bacteria, fungi or algae.

10. A method of treating a seawater system contaminated with microbes, the method comprising the step of adding to said system separately or together, a biocidally active amount of a THP salt and a biopenetrant, wherein the biopenetrant comprises a polymer of an unsaturated carboxylic acid, said polymer being terminated by vinylphosphonic acid (VPA) or having such monomers incorporated into the polymer backbone, thereby killing at least some of said microbes.

11. The method according to claim 10, wherein the THP salt is tetrakis(hydroxymethyl) phosphonium sulfate.

12. The method according to claim 10, wherein the THP salt is a tetrakis(hydroxymethyl) phosphonium phosphite, a tetrakis(hydroxymethyl) phosphonium bromide, a tetrakis(hydroxymethyl) phosphonium fluoride, a tetrakis(hydroxymethyl) phosphonium chloride, a tetrakis(hydroxymethyl) phosphonium phosphate, a tetrakis(hydroxymethyl) phosphonium carbonate, a tetrakis(hydroxymethyl) phosphonium formate, a tetrakis(hydroxymethyl) phosphonium citrate, a tetrakis(hydroxymethyl) phosphonium borate or a tetrakis(hydroxymethyl) phosphonium silicate.

13. The method according to claim 10, wherein the polymer of the biopenetrant is polyacrylate polymer.

14. The method according to claim 13, wherein the polyacrylate polymer has a molecular weight of about 4000.

15. The method according to claim 10, wherein the proportion of the VPA polymer to THP salt is from 1% to 50% by weight, relative to the total weight of the composition.

16. The method according to claim 15, wherein the proportion is from 1% to 25% by weight, relative to the total weight of the composition.

17. The method according to claim 16, wherein the proportion is from 1% to 5% by weight, relative to the total weight of the composition.

18. The method of claim 10, wherein the microbes are bacteria, fungi or algae.

* * * * *